(12) United States Patent
Berntsen et al.

(10) Patent No.: US 11,933,170 B2
(45) Date of Patent: Mar. 19, 2024

(54) WELL TESTING UNDER FULL FIELD PRODUCTION

(71) Applicant: Seabed Separation AS, Trondheim (NO)

(72) Inventors: Jon Sigurd Berntsen, Porsgrunn (NO); Asle Jostein Hovda, Jakobsli (NO); Idar Olav Grytdal, Ranheim (NO)

(73) Assignee: Seabed Separation AS, Trondheim (NO)

( * ) Notice: Subject to any disclaimer, the term of this patent is extended or adjusted under 35 U.S.C. 154(b) by 332 days.

(21) Appl. No.: 17/421,881

(22) PCT Filed: Jan. 28, 2020

(86) PCT No.: PCT/NO2020/050015
§ 371 (c)(1),
(2) Date: Jul. 9, 2021

(87) PCT Pub. No.: WO2020/159377
PCT Pub. Date: Aug. 6, 2020

(65) Prior Publication Data
US 2022/0106877 A1 Apr. 7, 2022

(30) Foreign Application Priority Data

Jan. 28, 2019 (NO) .................................. 20190101

(51) Int. Cl.
| | | |
|---|---|---|
| E21B 49/08 | (2006.01) | |
| B01D 17/02 | (2006.01) | |
| B01D 17/12 | (2006.01) | |
| B01D 19/00 | (2006.01) | |
| E21B 43/34 | (2006.01) | |
| G01N 33/28 | (2006.01) | |

(52) U.S. Cl.
CPC ........ *E21B 49/087* (2013.01); *B01D 17/0214* (2013.01); *B01D 17/12* (2013.01); *B01D 19/0063* (2013.01); *E21B 43/35* (2020.05); *G01N 33/2823* (2013.01)

(58) Field of Classification Search
CPC ... E21B 49/087; E21B 43/35; B01D 17/0214; B01D 17/12; B01D 19/0063; G01N 33/2823
See application file for complete search history.

(56) References Cited

U.S. PATENT DOCUMENTS 6,561,041 B1 * 5/2003 Eck .................... E21B 47/10
73/861.04
9,827,509 B2 11/2017 Skovholt
(Continued)

FOREIGN PATENT DOCUMENTS

NO 20170631 A1 10/2018
NO 20170632 A1 10/2018

OTHER PUBLICATIONS

International Search Report and Written Opinion dated Mar. 26, 2020 for International Patent Application No. PCT/NO2020/050015.

*Primary Examiner* — Taras P Bemko
(74) *Attorney, Agent, or Firm* — Alix, Yale & Ristas, LLP (57) ABSTRACT

Method and system for well testing under full field production comprising isolating well flow from one of multiple wells and running the well flow through a dedicated test slug suppression and gas removal unit and at least one isolated and dedicated inclined tubular separator for testing.

10 Claims, 5 Drawing Sheets

(56) References Cited

U.S. PATENT DOCUMENTS

| | | | | |
|---|---|---|---|---|
| 2003/0136185 A1* | 7/2003 | Dutton | ............... | E21B 49/0875 |
| | | | | 73/861.04 |
| 2004/0144543 A1* | 7/2004 | Appleford | ............... | E21B 34/04 |
| | | | | 166/336 |
| 2010/0214120 A1* | 8/2010 | Means | ................ | E21B 49/008 |
| | | | | 700/282 |
| 2014/0137642 A1* | 5/2014 | Henry | ................ | E21B 21/063 |
| | | | | 73/152.29 |
| 2015/0226051 A1* | 8/2015 | Machado | ............... | E21B 47/10 |
| | | | | 166/250.03 |
| 2017/0167906 A1* | 6/2017 | Henry | ................ | G01F 1/8468 |
| 2017/0219403 A1 | 8/2017 | Henry et al. | | |
| 2018/0252080 A1* | 9/2018 | Vilstrup | ................ | E21B 47/10 |
| 2020/0018146 A1 | 1/2020 | Strommen et al. | | |
| 2020/0139266 A1 | 5/2020 | Daasvatn et al. | | |
| 2020/0378234 A1 | 12/2020 | Daasvatn | | |
| 2022/0010677 A1* | 1/2022 | Duncan | ................ | E21B 43/12 |

\* cited by examiner

WELL TESTING UNDER FULL FIELD PRODUCTION

BACKGROUND

The disclosed embodiments relate to a method for well testing under full field production and to a system for well testing under full field production.

Flow allocation is a big issue for all parties involved due to the large financial impact that will result from the outcome. It is especially challenging when various fields with various owners and owner groups are producing into the same infrastructure. Well testing will then be the single most important factor in allocating how much volumes are produced from which fields.

The key challenges with the current practice are that:
  Best Practice is considered to be within a +/−5% band when it comes to produced volumes.
  Owners of the pre-existing infrastructure will build in their own safety margins on top of the best practice numbers to ensure they do not lose out.
  When maximizing flow on the processing facility, the owner of the processing facility can adjust the allocation in their favour.

In addition, the cost of such production well testing is very expensive due to lost production from other wells during the well test period.

When producing from a field with more than one well there will be a requirement to perform individual well testing to verify how much the various wells are contributing with regards to the various phases; oil, gas and water. For subsea operations this is normally conducted by using multi-phase flow meter, but limited to one well at time, hence lost production during test time.

The ambition is to conduct well testing at conditions as close to real life production conditions, but a deviation as high as +/−5% in flow volumes are still consider as best practise.

A typical subsea set-up is that several producing wells are fed into one common subsea manifold station before it is transported back to a topside processing facility in one common pipeline and thus mixing the flow from all wells feeding into the manifold. This processing facility can be a production platform, an FPSO, a subsea processing facility or a land terminal. Such well testing operations of subsea wells are normally performed at the processing facility.

The standard procedure will then be to shut down all the wells and produce from one well at a time, until all the necessary tests have been performed. A typical scenario includes these steps:
  1. Shut down all wells apart from the one set for testing or shut down all wells and open one well for testing.
  2. Allow the production from the test well to stabilize through the transport system back to the processing facility—approx. 12 hours (ex 00.00-12.00)
  3. Test 1st choke setting, measure flow volume and allow to settle for test of $2^{nd}$ choke settings—approx. 6 hours (ex. 12.00-18.00).
  4. Test $2^{nd}$ choke setting, measure flow volume and allow to settle for test of $3^{rd}$ choke settings—approx. 6 hours (ex. 18.00-24.00).
  5. (Test $3^{rd}$ choke setting and measure flow volume—approx. (ex. 24.00))

I.e. testing one production well takes 24 hrs.

Figure 1:
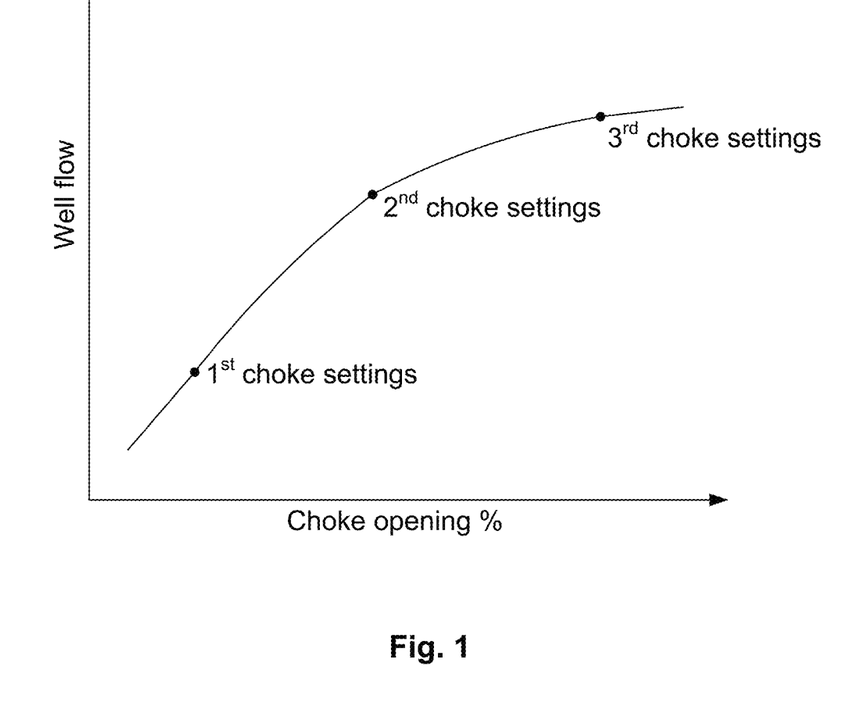
FIG. 1 is an example of a flow allocation curve.

The test results are then used to draw a function line representing the production flow vs. choke opening, as shown in FIG. 1. This function line is next used to allocate production to individual wells and fields.

There is accordingly a need for a system and method for well testing under full field production where one does not have to shut down the other production wells while testing one well.

SUMMARY

Provided herein is a method and system for well testing under full field production that partly or entirely solves the above-mentioned drawbacks of prior art.

Also provided is a method and system enabling the use of parts of separator components of a production system to be used for testing.

Also provides is a method and system enabling one out of a multiple wells to be isolated and tested while contributing to production from a field.

Also provided is a method and system removing the need for shutting down wells during testing.

Also provided is a method and system where testing can be performed without production losses.

Also provided is a method and system enabling more correct distribution of values from production.

A Also provided is a method and system providing improved operating conditions of the overall production system.

The disclosed embodiments relate to the use of multiple inclined tubular separators, as disclosed in WO2014096330, WO2014096356 and especially WO2018063007, all in the name of the applicant, the content of all included herein by reference.

Accordingly, the disclosed embodiments are related to the use of a separator system including multiple inclined tubular separators comprising:
  an elongated outer tube and an elongated inner tube, where the inner tubular tube is arranged inside the outer tube,
  where oil well substances are introduced into an end of the inner tube via a feed section passing through the outer tube and into the inner tube,
  and where the inner tube comprises multiple holes or slots arranged in a longitudinal direction,
  where the inclination of the tubular separator facilitates separation of the oil well substances into lower density substances and higher density substances. In the inclined tubular separators, lower density substances by buoyancy drift upwards through the slots or holes and exit via an upper outlet in the outer tube, and higher density substances sink downwards through the slots or holes and by gravitation exit via a lower outlet in the outer tube.

The disclosure further takes basis in that a slug suppression and gas removal unit (SSGR unit) is arranged between the well and the inclined oil and water separator system.

The disclosed embodiments further may be provided with a sand trap system between the gas removal unit and the inclined oil and water separator system.

The disclosed embodiments provide a new approach that will level the playing field by proving a system and method enabling testing and allocating flow on individual wells while maintaining normal flow from the other wells. This lowers the threshold for conducting production testing significantly, and thus enabling shorter interval between well testing operations. The production testing will have limited effects on the production to avoid loss of production during testing.

The disclosed embodiments include means for isolating one of the multiple wells and perform test of the well flow of the isolated well.

To perform the test of the well flow from the isolated well the disclosed embodiments make use of a dedicated test slug suppression and gas removal unit for separation of gas and where a gas meter is arranged to measure the produced gas volume ($m^3/h$) from the separated well.

The disclosed embodiments are further based on utilizing at least one of the multiple inclined tubular separators for testing of the well flow from the isolated well. The present invention is for this provided with means for isolating at least one of the multiple inclined tubular separators from the remaining tubular separators, providing at least one isolated and dedicated inclined tubular test separator, such that the well flow from the isolated well can be run through the at least one dedicated inclined tubular test separator while the remaining inclined tubular separators are used for the well flow from the other wells, which will provide normal production.

In connection with the at least one dedicated inclined tubular test separator is arranged an oil meter and water meter for measuring the produced oil and water volumes ($m^3/h$), respectively, from the well flow from the isolated well.

The disclosed embodiments are further arranged such that the production (gas, oil, water) from the well flow of the tested isolated well is added to the production (gas, oil, water) from the other wells further downstream of the test facility.

The disclosed embodiments can further comprise at least one dedicated test sand trap and means for directing the well flow of the isolated well for measurement of sand content in the well flow.

Accordingly, a method for individual well testing under full field production comprises a step of isolating well flow from one of the multiple wells and isolating at least one of the inclined tubular separators from the remaining inclined tubular separators and dedicating the at least one isolated inclined tubular separator for testing.

The method further comprises a step of running the well flow from the isolated well through a dedicated test slug suppression and gas removal unit and the at least one isolated and dedicated inclined tubular separator for a test period and running well flow from the other wells through the production slug suppression and gas removal unit and remaining inclined tubular separators as during normal production.

The method further comprises a step of measuring produced gas, oil and water volumes ($m^3/h$) for the isolated well in the test period.

The method further comprises a step of adding the respective produced gas, oil and water for the isolated well from the dedicated test slug suppression and gas removal unit and the at least one isolated and dedicated inclined tubular separator to the respective produced gas, oil and water for the other wells from the production slug suppression and gas removal unit and the remaining inclined tubular separators.

The method further comprises a step of removing the isolation of the tested well and the at least one dedicated inclined tubular separator when the test period is ended, returning the production system to normal operation.

The method can comprise repeating the mentioned steps for the different multiple wells.

The method can further comprise a step of running the well flow from the isolated well through at least one dedicated test sand trap upstream of the at least one dedicated inclined tubular separator and measuring content of sand in the well flow.

The method can further comprise allowing a stabilizing period initially in the test period, i.e. after the well flow from the isolated well is directed through the dedicated test slug suppression and gas removal unit and the at least one isolated and dedicated inclined tubular separator, before performing measurements of produced gas, oil and water volumes ($m^3/h$) from the well flow of the isolated well.

The disclosed embodiments provide full certainty and assurance that the production allocation numbers are correct and relevant.

The disclosed embodiments further provide a solution where well testing is conducted at optimum conditions.

The disclosed embodiments provide reduction of the uncertainty between operational partners.

The disclosed embodiments thus reduce conflict level between different operators at the same production field.

The disclosed embodiments provide a solution enabling production from all fields while conducting well testing operations.

The disclosed embodiments provide a solution having limited effects on the production and avoids loss in production during testing.

The disclosed embodiments provide improved financial performance.

BRIEF DESCRIPTION OF THE DRAWINGS

The present invention will below be described in further detail with references to the attached drawings, where.

DETAILED DESCRIPTION

Figure 2A:
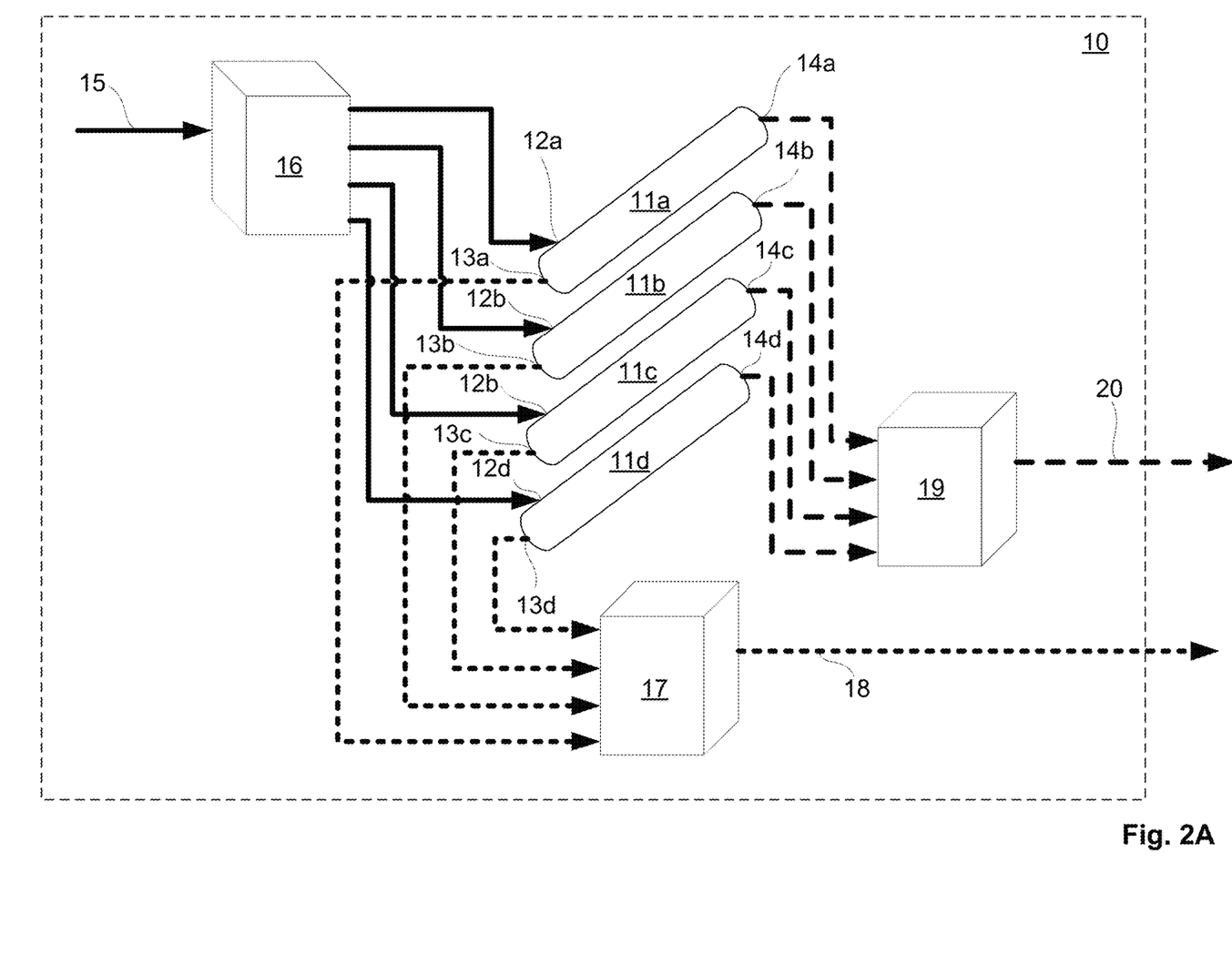
FIGS. 2A and 2B are principle drawings of prior art inclined tubular separator system.
Figure 2B:
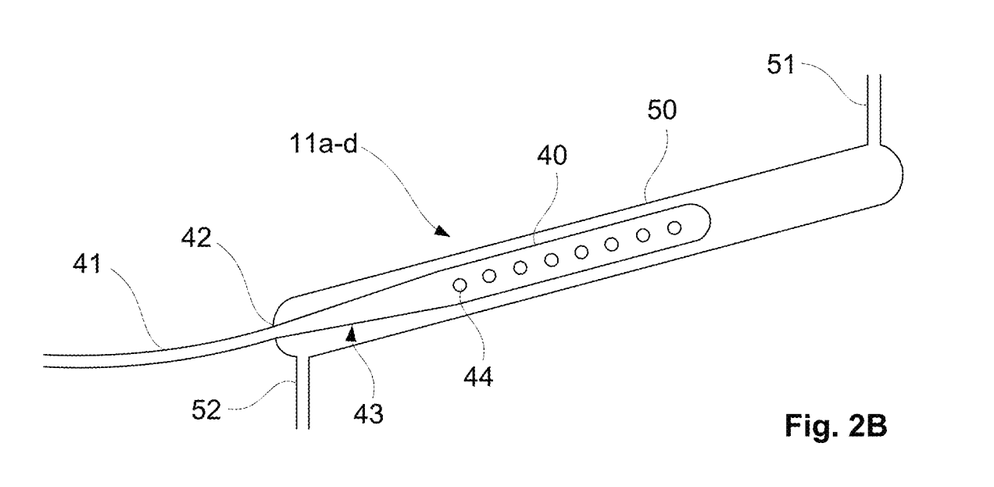

Reference is now made to FIGS. 2A and 2B which are principle drawings of a separator system according to prior art, as described in WO2014096330, WO2014096356 and especially WO2018063007, illustrated by a separator system 10 comprising four interconnected inclined tubular separators 11a-d using gravity as the separating force.

Each inclined tubular separator 11a-d has a respective inlet 12a-d in a lower section of the inclined tubular separator 11a-d, and a respective outlet 13a-d also located in the lower/bottom section of the inclined tubular separator 11a-d. A respective outlet 14a-d is located in an upper section of the inclined tubular separator 11a-d.

The separator system is supplied with fluid from an oil well (not shown) by a pipe 15 and via an input manifold 16 which distributes the fluid to the respective inclined tubular separators 11a-d and interconnecting the inclined tubular separators 11a-d in a parallel fashion, or in series, or in a combination of parallel and serial configurations. There is further arranged a first output manifold section 17 interconnecting the outlets 13a-d in a parallel fashion, or in series, or in a combination of parallel and serial configurations to an outlet pipe 18.

There is further arranged a second output manifold section 19 interconnecting the outlets 14a-d from the inclined tubular separators 11a-d, in a parallel fashion, or in series, or in a combination of parallel and serial configurations to an outlet pipe 20, with respect to the number of phases the separator system is adapted and manufactured to separate.

The fluid streaming through the pipe 15 is connected in parallel to inlets 12a-d of the respective inclined tubular separators 11b-d by the input manifold 16 thereby providing a sufficient separator capacity for separating oil from water, for example. The oil phase is transported out of the separator system via the respective outlets 14a-d of the respective inclined separators 11a-d, and in the output manifold section 19 these outlets are connected together and are connected to the (oil) outlet pipe 20 of the separator system. The water is transported out of each respective inclined tubular separators 14a-d being configured to separate oil from water via the outlets 13a-d being located in the bottom section of the inclined separator system first output manifold 17 and to the outlet (water) pipe 18.

The routing provided by pipe connections in the output manifold section 17, is reflected in the output manifold section 19. The routing of pipes reflects the properties of the incoming fluids from an oil well, while the routing in the output manifold section 19 reflects how many fluid phases that are to be separated and how different fluid phases will be combined. Therefore, there is a functional relationship between the routing of pipes in the output manifold section 17 and the output manifold section 19, but not necessary as a one to one mapping of the configuration of the respective pipes in each respective manifold section.

Reference is now made to FIG. 2B, showing details of the interior of the inclined tubular separators 11a-d. The inclined tubular separators 11a-d have an inner elongated tube 40 located centred inside an outer elongated tube 50, wherein the inner tube 40 is in fluid communication with the input manifold 17 or pipe 15 via the respective inlets 12a-d and via a curved pipe 41 extending out of the outer tube 50 via an opening 42 in a side wall of the outer tube 50 at a lower section of the inclined tubular separator 11a-d. The inner tube 40 exhibits a conical shaped part 43 at the lower/inlet part thereof expanding in width from the curved pipe 41 to a final width of 18" within the inner tube 40. The walls of the inner tube 40 are further perforated with a plurality of holes or slots 44, and the inner tube 40 is terminated and closed at upper end thereof. The outer tube 50 has a first outlet opening 51 arranged at upper end thereof connected to the outlet 14a-d and a second outlet opening 52 at lower end thereof connected to the outlet 13a-d. The conical shape will reduce the velocity of the fluid before passing the inner tube holes or slots 44.

There will further be arranged a production slug suppression and gas removal unit 100 (SSGR) between the wells and the separator system 10/multiple inclined tubular oil and water separators 11a-d.

Further details of this separator system can be found in WO2014096330, WO2014096356 and especially WO2018063007.

Figure 3A:
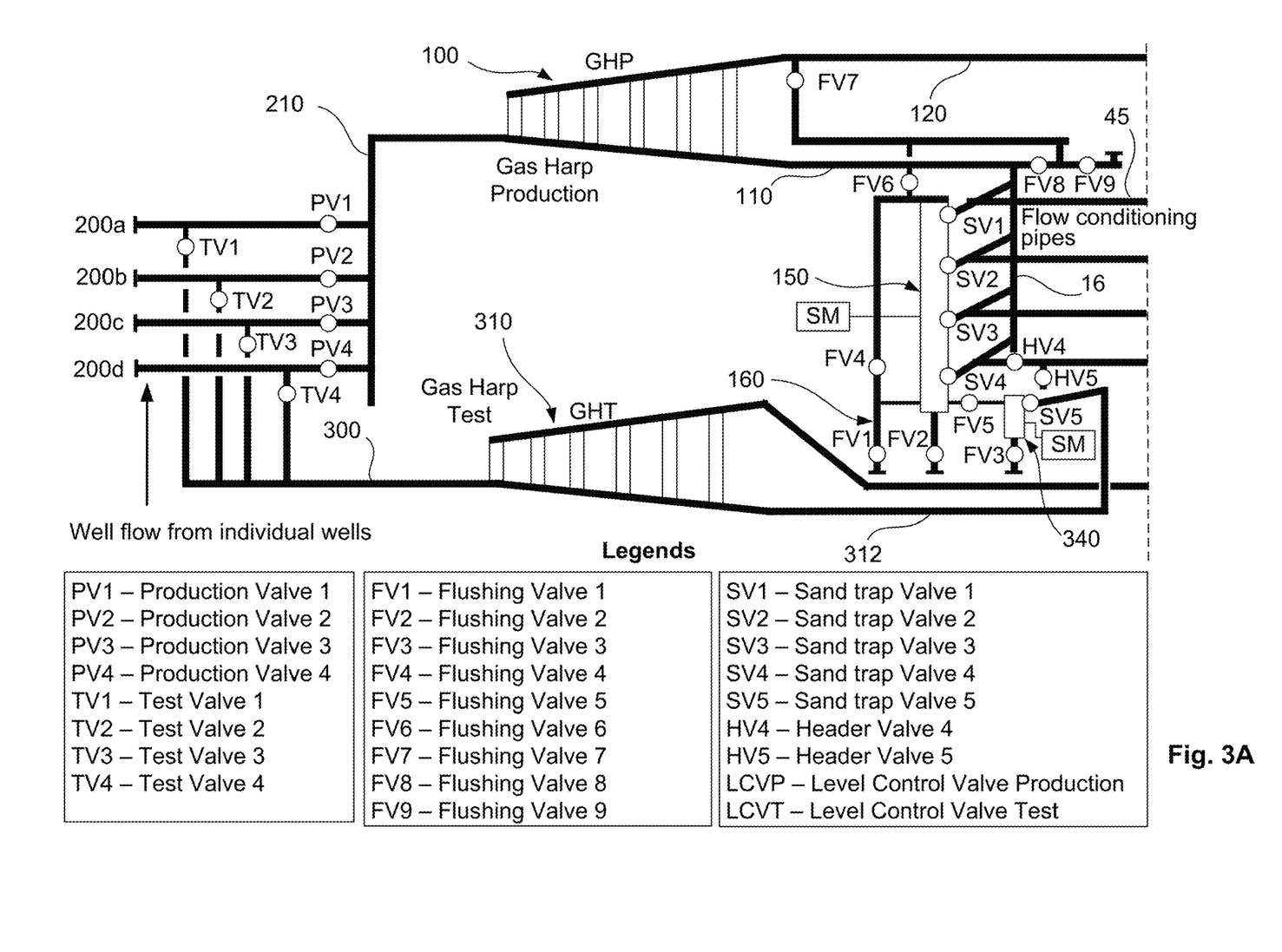
FIG. 3A is a principle drawing of a first portion of a production system with a test system according to the disclosure.
Figure 3B:
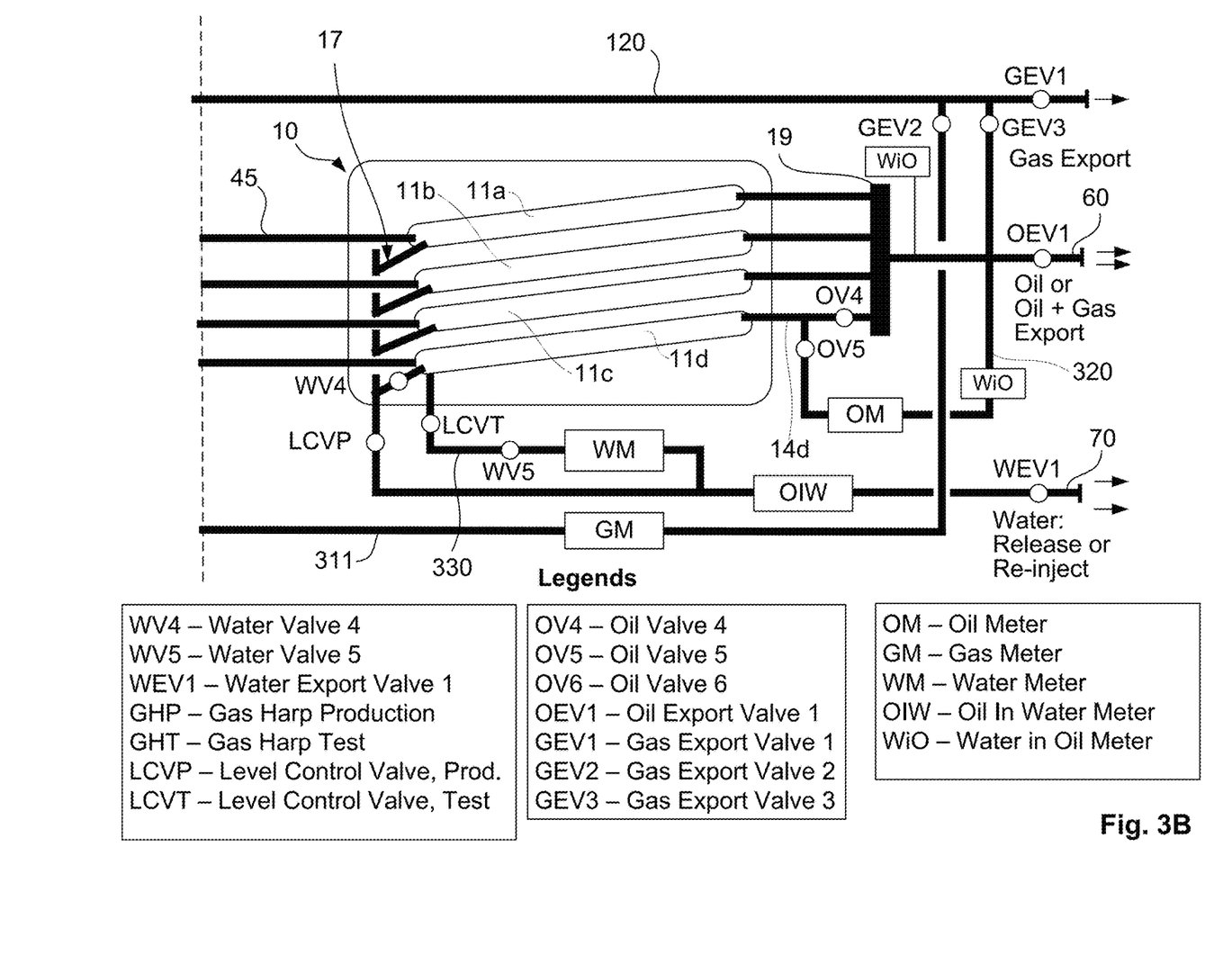
FIG. 3B is a principle drawing of a second portion of the production system with a test system according to the disclosure.

Reference is now made to FIG. 3 which is a principle drawing of a system according to the disclosure. The inventive embodiments will make use of the above described separator system 10 for oil and water separation from well flows, while production SSGR 100 will be used for separating gas from well flows.

In FIG. 3 is shown principle drawing of a normal production system with four individual wells 200a-d connected to a common pipeline 210 via respective controllable production valves PV1-PV4, which common pipeline 210 is connected to an inlet of the production SSGR 100, also known as a Gas harp, at the other side. Oil and water outlet 110 of the production SSGR 100 is connected to the input manifold section 16 of the inclined tubular separator system 10. As shown in FIG. 3 there are used flow conditioning pipes 45 between the input manifold section 17 and the respective inclined separator 11a-d as described in WO2018063007.

The production SSGR 100 will provide a gas output 120 for gas export and the separator system 10 will provide an oil or oil and gas output 60 for oil or oil and gas export, as well as a water output 70 for water export, release or reinjection, which is well known for a skilled person and requires no further description herein.

According to a further embodiment, the production system may further be provided with a production sand trap 150 in connection with the input manifold 16, and in connection with the separate inclined tubular separators 11a-d via sand trap valves SV1-4. The production sand trap 150 will be connected to a sand trap jetting system 160 comprising a number of flushing valves FV1-9 for removal of sand from the production sand trap 150.

The system comprises a test system enabling the use of at least one of the inclined tubular separators for testing.

The test system comprises controllable test valves TV1-TV4 arranged in front of the production valves PV1-PV4 for the respective wells 200a-d enabling isolation of the well flow from individual wells to a test pipeline 300. The test system further comprises a dedicated test SSGR 310 corresponding to the production SSGR 100 of the production system and the inlet of the test SSGR 310 is connected to the test pipeline 300. Gas outlet 311 of the dedicated test SSGR 310 is connected to the gas outlet 120 of the production SSGR via a controllable valve GEV2. There is further arranged a gas meter GM in connection with the gas outlet 311 for the test SSGR 310 for measuring the produced gas volume ($m^3/h$) in a test period.

Oil and water outlet 312 of the dedicated test SSGR 310 is connected to respective inlets 12a-d of the respective inclined tubular separator 11a-d by means of a controllable header valve HV5. In the shown example the connection is made in connection with the flow conditioning pipe 45, but the connection may also be directly to the inlet 12a-d.

The test system further comprises an oil bypass section 320 arranged in connection with the output manifold section 19, enabling isolation of the respective outlets 14a-d of the respective inclined tubular separator 11a-d into the oil bypass section 320 via a controllable oil valve OV5, as well as controllable oil valve OV4 for closing the connection to the output manifold section 19. The oil bypass section 320 is at the other end connected to the oil or oil and gas outlet 60. An oil meter OM is arranged in connection with the oil bypass section 320 for measuring produced oil volume ($m^3/h$) in a test period.

The test system further comprises a water bypass section 330 arranged in connection with the first output manifold section 17, enabling isolation of the respective outlet 13a-d of the respective inclined tubular separator 11a-d into the water bypass section 330 via a controllable water valve WV5, as well as controllable water valve WV4 for closing the connection to the first output manifold section 17. The water bypass section 330 is at the other end connected to the water outlet 70 for water export. A water meter OM is arranged in connection with the water bypass section 330 for measuring produced water volume (m³/h) in a test period.

According to a further embodiment of the test system further comprises at least one dedicated test sand trap 340 arranged in connection with the inlet manifold section 16, enabling isolation of the respective inlet 12a-d of the respective inclined tubular separator 11a-d into the at least one dedicated test sand trap 340 via a controllable sand trap valve SV5, as well as controllable flushing valve FV5 for closing the connection to the production sand trap 150. There is further arranged means MS for measuring sand content in the well flow from the isolated well in connection with the dedicated test sand trap 340. The means MS for measuring sand content may be a level meter and/or rate meter. It should be mentioned that similar means MS are also arranged in connection with the production sand trap 150.

Below will be described how a well test for an individual well 200a-d can be performed with reference to FIG. 3. The test procedure will be related to the system described above.

The first step is to isolate the test system from the production system to enable production testing for one well 200a-d. A first step will be to verify that valves SV4 and FV3 related to the dedicated test sand trap 340 are closed. Next is to ensure that the dedicated test sand trap 340 is activated by opening valve SV5.

The next step is to open water valve WV5, and ensure that gas export valve GEV1, oil export valve OEV1 and water export valve WEV1 are open.

The next step is to enable flow from the test system back into the production system. This is achieved by opening gas export valve GEV2 allowing gas from the dedicated test SSGR 310 to be exported, followed by opening oil valve OV5 allowing separated oil in the inclined tubular separator 11d to flow into the oil bypass section 320 and closing oil valve OV4 preventing separated oil from the inclined tubular separator 11d to enter the output manifold 19 of the separator system 10.

The next step is to shift the interface level control for the inclined tubular separator 11d from the interface level control valve LCVP, used in production, to interface level control valve LCVT used for test. When the interface control valve LCVT is confirmed operational, the water valve WV4 is closed.

The inclined tubular separator 11d is now fully controlled by interface level control valve LCVT and both water and oil exits via test outlets and meters. The inclined tubular separator 11d is now isolated and a dedicated inclined tubular test separator that can be used for a test period.

The system is now ready to shift production to test mode for a chosen well. For the further description well 200a is chosen as an example.

The header valve HV5 is opened and as well as test valve TV1, and production valve PV1 as well as header valve HV4 is closed, resulting in that well flow from well 200a is now isolated and routed for a well test via the dedicated test SSGR 300 and oil and water separation in the isolated and dedicated inclined tubular separator 11d.

Following a 15-30 minutes stabilising period (approximate), well testing can be performed. In the test period rates can be measured by the WM, OM and GM meters for water, oil and gas, respectively for the well 200a, as well as sand content by the SM.

There is further a requirement in such systems that oil in water devices OIW are arranged on the test line downstream of the WM and downstream in the production line for mass balance control.

This test configuration will limit production losses to when multi-rate tests are carried out. The initiation and termination of a test can take place without production losses.

The disclosed embodiments provide great financial potential. For a multi-well subsea production system the financial improvement potential will be considerable.

Key assumptions are;
1. 60 000 bbls/day oil production
2. 4 wells—one day per well
3. One common manifold and export line to processing hub
4. 2 annual well test campaigns
5. 60 USD/bbls (á 8.0 USD/NOK)

Further, the embodiments provide improved production numbers due to reducing the amount of lost production during the reduced production capacity during a well testing campaign.

This will result in an annual gain of:
(¾ wells)×60 000 bbls/day×(4 days testing)×(60 USD×8 USD/NOK)×(2 test periods)=172.8 MNOK. By prior art 3 of 4 well will not produce.

This will further result in gain from improved Best Practice:

By example, if 1% improved allocation performance is achieved: 60 000 bbls/day×360 days×(60 USD/bbl×8 USD/NOK)×1%=103.7 MNOK Accordingly, increased operating revenues is achieved, in addition to a more correct distribution of the values.

In addition to the above, the test system may be used for redundancy in case of maintenance or error in the production system. I.e. if there is an error or requirement of maintenance on the production SSGR 100 the dedicated test SSGR 310 may be used instead. The system can further be provided with means (not shown) for connecting the oil and water outlet of the dedicated test SSGR 310 to the input manifold 16 of the separator system 10.

Figure 4:
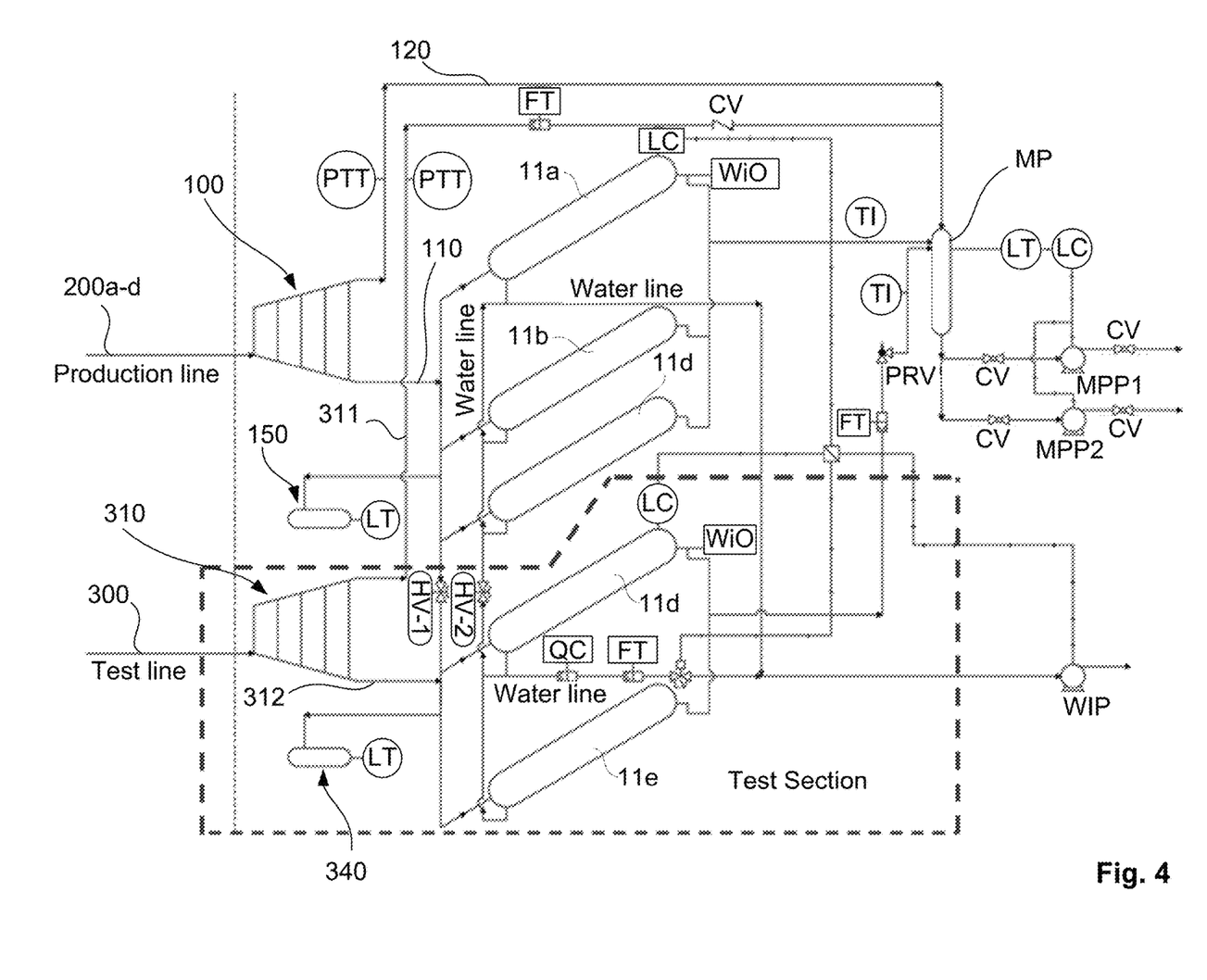
FIG. 4 is a principle drawing of controlling of a system according to the disclosure.

Reference is now made to FIG. 4 which is a principle drawing of how the system is controlled. FIG. 4 further shows an example of the use of two isolated and dedicated inclined tubular separators 11d-e for testing. In the Figure is shown PTT—Pressure transmitter, LC—Level Controller, LV—Level Valve (at water side of test section), TI—Temperature Indicator, QC—Quality Control (oil in water analyzer), WiO Water in Oil analyzer, LT—Level Transmitter, FT—Flow Transmitter, PRV—Pressure Regulating Valve, HV—Header valve (isolation valve), CV—Control valve, and MP—Mixing pipe.

In normal operation, i.e. production, all valves are open and multiphase pump(s) (MPP) and water inject pump (WIP) are controlled by respective level controllers (LC).

In test mode the header valves HV-1, HV-2 are closed to separate between production in some of the inclined tubular separators 11a-e and testing in at least one of the inclined tubular separators 11a-e. In the illustrated example two inclined separators 11d-e are used for testing.

The WIP is operated in cascade control with signals from LC in the production part and signal from LC from the test section via a level valve (LV). Accordingly, there are two separate (individual) systems, in the form of the production part and test section, using the same pump.

In the test section a pressure regulating valve (PRV) will act as a pressure maintaining valve, i.e. that the pressure in the test section is independent of the pressure in the production part. The PRV will «hold» the pressure in the test section and let through gass/fluid such that the pressure at donwstream side of the pressure regulating valve does not increase.

Further, in test mode quality control instruments and FT flow meters are activated.

Accordingly, FIG. 4 provides further details of the controlling of the system according to the disclosure, as shown in FIG. 3.

The invention claimed is:

1. A method for well testing under full field production, wherein well flow from multiple wells (200a-200d) is run through a production system during full field production, the production system comprising a production slug suppression and gas removal unit (100) and a separator system (10) comprising multiple interconnected inclined tubular separators (11a-11e) for separating gas, oil and water from the well flow, comprising the steps of:
   (a) isolating well flow from one of the multiple wells (200a-200d) to define an isolated well and isolating at least one of the inclined tubular separators (11a-11e) from the multiple interconnected inclined tubular separators (11a-11e) and dedicating the at least one isolated inclined tubular separator (11a-11e) for testing,
   (b) running the well flow from the isolated well (200a-200d) through a dedicated test slug suppression and gas removal unit (310) and the at least one isolated and dedicated inclined tubular separator (11a-11e) to initiate a test period,
   (c) running well flow from non-isolated wells (200a-200d) through the production slug suppression and gas removal unit (100) and non-isolated inclined tubular separators (11a-11e),
   (d) measuring volumes of gas, oil and water produced for the isolated well (220a-200d),
   (e) adding the respective gas, oil and water produced for the isolated well (220a-200d) from the dedicated test slug suppression and gas removal unit (310) and the at least one isolated and dedicated inclined tubular separator (11a-11e) to the respective gas, oil and water produced for the non-isolated wells (200a-200d) from the production slug suppression and gas removal unit (100) and the non-isolated inclined tubular separators (11a-11e), and
   (f) removing the isolation of the isolated well (200a-200d) and at least one isolated and dedicated inclined tubular separator (11a-11e) to end the test period.

2. The method according to claim 1, comprising repeating steps (a)-(f) for different wells (200a-200d).

3. The method according to claim 2, comprising running the well flow from the isolated well (200a-200d) through at least one dedicated test sand trap (340) and measuring content of sand in the well flow.

4. The method according to claim 2, comprising allowing a stabilizing period after step (b) and prior to step (d) of measuring volumes of gas, oil and water produced for the isolated well (220a-200d).

5. The method according to claim 1, comprising running the well flow from the isolated well (200a-200d) through at least one dedicated test sand trap (340) and measuring content of sand in the well flow.

6. The method according to claim 5, comprising allowing a stabilizing period after step (b) and prior to step (d) of measuring volumes of gas, oil and water produced for the isolated well (220a-200d).

7. The method according to claim 1, comprising allowing a stabilizing period after step (b) and prior to step (d) of measuring volumes of gas, oil and water produced for the isolated well (220a-200d).

8. A system for well testing under full field production, wherein well flow from multiple wells (200a-d) is run through a production system during full field production, the production system comprising a production slug suppression and gas removal unit (100) and a separator system (10) comprising multiple interconnected inclined tubular separators (11a-11e) for separating gas, oil and water from the well flow, comprising:
   (a) controllable units (PV1-PV4, TV1-TV4) for isolating well flow from one of the multiple wells (200a-200d) from well flow of the non-isolated wells (200a-200d),
   (b) a dedicated test slug suppression and gas removal unit (310) for separation of gas from the well flow from the isolated well (200a-200d),
   (c) controllable units (HV1-HV2, HV4-HV5, WV4-WV5, LCVT, OV4-OV5) for isolating at least one of the inclined tubular separators (11a-11e) from the multiple interconnected inclined tubular separators (11a-11e) and dedicating the at least one isolated inclined tubular separator (11a-11e) for separation of the well flow from the isolated well (200a-200d), and
   (d) units (GM, OM, WM) for measuring gas, oil and water volumes ($m^3/h$) produced for the isolated well (220a-d),
   wherein the units for isolating well flow (PV1-PV4, TV1-4) and units for isolating at least one of the inclined tubular separators (HV1-HV2, HV4-HV5, WV4-WV5, LCVT, OV4-OV5) collectively allow the well flow from the isolated well (200a-200d) to be run through the dedicated test slug suppression and gas removal unit (310) and the at least one isolated and dedicated inclined tubular separator (11a-11e) for a test period while well flow from the non-isolated wells (200a-200d) is run through the production slug suppression and gas removal unit (100) and multiple interconnected inclined tubular separators (11a-11e),
   and comprising outlets, lines or both (311, 320, 330) for adding the respective produced gas, oil and water for the separated well (220a-200d) from the dedicated test slug suppression and gas removal unit (310) and the at least one isolated and dedicated inclined tubular separator (11a-11e) to the respective produced gas, oil and water for the non-isolated wells (200a-200d) from the production slug suppression and gas removal unit (100) and the multiple interconnected inclined tubular separators (11a-11e).

9. The system according to claim 8, comprising at least one dedicated test sand trap (340) and units (SV4-SV5) for running the well flow from the isolated well (200a-200d) through the at least one dedicated test sand trap (340).

10. The system according to claim 9, comprising a unit (MS) for measuring sand content in the at least one dedicated test sand trap (340).

* * * * *